United States Patent [19] [11] Patent Number: 4,851,512
Miyaji et al. [45] Date of Patent: Jul. 25, 1989

[54] NOVEL HUMAN INTERLEUKIN-2 POLYPEPTIDE DERIVATIVE

[75] Inventors: Hiromasa Miyaji, Tokyo; Seiga Itoh, Kanagawa, both of Japan

[73] Assignee: Kyowa Hakko Kogyo Co., Ltd., Tokyo, Japan

[21] Appl. No.: 911,811

[22] Filed: Sep. 26, 1986

[51] Int. Cl.$^4$ .................. C07K 13/00; C12P 21/00
[52] U.S. Cl. .................... 530/351; 435/68; 424/85.2
[58] Field of Search ............ 530/351; 435/68; 424/85.2

[56] References Cited

U.S. PATENT DOCUMENTS 4,636,463 1/1987 Altman et al. .................. 435/7

FOREIGN PATENT DOCUMENTS 091539 10/1983 European Pat. Off. .
0136489 4/1985 European Pat. Off. .

Primary Examiner—Blondel Hazel
Attorney, Agent, or Firm—Nixon & Vanderhye

[57] ABSTRACT

Novel human IL-2 polypeptide derivatives characterized by deletion of at least one amino acid from the amino acid sequence of the human IL-2 polypeptide, recombinant plasmids containing DNAs coding for the above derivatives, microorganisms harboring these plasmids and methods of producing the above derivatives in these microorganisms are provided.

3 Claims, 5 Drawing Sheets

FIG. 1

```
CACTCTCTTTAATCACTACTCACAGTAACCTCAACTCCTGCCACAATGTACAGGATGCAA
                                                 MetTyrArgMetGln
                                                      -20
                                                        1
CTCCTGTCTTGCATTGCACTAAGTCTTGCACTTGTCACAAACAGTGCACCTACTTCAAGT
LeuLeuSerCysIleAlaLeuSerLeuAlaLeuValThrAsnSerAlaProThrSerSer
         -10                                    -1  1

TCTACAAAGAAAACACAGCTACAACTGGAGCATTTACTGCTGGATTTACAGATGATTTTG
SerThrLysLysThrGlnLeuGlnLeuGluHisLeuLeuLeuAspLeuGlnMetIleLeu
         10                                   20

AATGGAATTAATAATTACAAGAATCCCAAACTCACCAGGATGCTCACATTTAAGTTTTAC
AsnGlyIleAsnAsnTyrLysAsnProLysLeuThrArgMetLeuThrPheLysPheTyr
         30                                   40

ATGCCCAAGAAGGCCACAGAACTGAAACATCTTCAGTGTCTAGAAGAAGAACTCAAACCT
MetProLysLysAlaThrGluLeuLysHisLeuGlnCysLeuGluGluGluLeuLysPro
         50                                   60

CTGGAGGAAGTGCTAAATTTAGCTCAAAGCAAAAACTTTCACTTAAGACCCAGGGACTTA
LeuGluGluValLeuAsnLeuAlaGlnSerLysAsnPheHisLeuArgProArgAspLeu
         70                                   80

ATCAGCAATATCAACGTAATAGTTCTGGAACTAAAGGGATCTGAAACAACATTCATGTGT
IleSerAsnIleAsnValIleValLeuGluLeuLysGlySerGluThrThrPheMetCys
         90                                  100

GAATATGCTGATGAGACAGCAACCATTGTAGAATTTCTGAACAGATGGATTACCTTTTGT
GluTyrAlaAspGluThrAlaThrIleValGluPheLeuAsnArgTrpIleThrPheCys
         110                                 120

CAAAGCATCATCTCAACACTGACTTGATAATTAAGTGCTTCCCACTTAAAACATATCAGG
GlnSerIleIleSerThrLeuThr
         130      133

CCTTCTATTTATTTAAATATTTAAATTTTATATTTATTGTTGAATGTATGGTTTGCTACC

TATTGTAACTATTATTCTTAATCTTAAAACTATAAATATGGATCTTTTATGATTCTTTTT

GTAAGCCCTAGGGGCTCTAAAATGGTTTCACTTATTTATCCCAAAATATTTATTATTATG

TTGAATGTTAAATATAGTATCTATGTAGATTGGTTAGTAAAACTATTTAATAAATTTGAT

AAATATAAAAAAAAAAAAAAAAAAAAAAAA
```

FIG. 5

```
                                                                  1
CACTCTCTTTAATCACTACTCACAGTAACCTCAACTCCTGCCACAGCACCTACTTCAAGT
                                                   AlaProThrSerSer
                                                                  1

TCTACAAAGAAAACACAGCTACAACTGGAGCATTTACTGCTGGATTTACAGATGATTTTG
SerThrLysLysThrGlnLeuGlnLeuGluHisLeuLeuLeuAspLeuGlnMetIleLeu
            10                                       20

AATGGAATTAATAATTACAAGAATCCCAAACTCACCAGGATGCTCACATTTAAGTTTTAC
AsnGlyIleAsnAsnTyrLysAsnProLysLeuThrArgMetLeuThrPheLysPheTyr
            30                                       40

ATGCCCAAGAAGGCCACAGAACTGAAACATCTTCAGTGTCTAGAAGAAGAACTCAAACCT
MetProLysLysAlaThrGluLeuLysHisLeuGlnCysLeuGluGluGluLeuLysPro
            50                                       60

CTGGAGGAAGTGCTAAATTTAGCTCAAAGCAAAAACTTTCACTTAAGACCCAGGGACTTA
LeuGluGluValLeuAsnLeuAlaGlnSerLysAsnPheHisLeuArgProArgAspLeu
            70                                       80

ATCAGCAATATCAACGTAATAGTTCTGGAACTAAAGGGATCTGAAACAACATTCATGTGT
IleSerAsnIleAsnValIleValLeuGluLeuLysGlySerGluThrThrPheMetCys
            90                                      100

GAATATGCTGATGAGACAGCAACCATTGTAGAATTTCTGAACAGATGGATTACCTTTTGT
GluTyrAlaAspGluThrAlaThrIleValGluPheLeuAsnArgTrpIleThrPheCys
           110                                      120

CAAAGCATCATCTCAACACTGACTTGATAATTAAGTGCTTCCCACTTAAAACATATCAGG
GlnSerIleIleSerThrLeuThr
           130      133

CCTTCTATTTATTTAAATATTTAAATTTTATATTTATTGTTGAATGTATGGTTTGCTACC

TATTGTAACTATTATTCTTAATCTTAAAACTATAAATATGGATCTTTTATGATTCTTTTT

GTAAGCCCTAGGGGCTCTAAAATGGTTTCACTTATTTATCCCAAAATATTTATTATTATG

TTGAATGTTAAATATAGTATCTATGTAGATTGGTTAGTAAAACTATTTAATAAATTTGAT

AAATATAAAAAAAAAAAAAAAAAAAAAAAA
```

NOVEL HUMAN INTERLEUKIN-2 POLYPEPTIDE DERIVATIVE

BACKGROUND OF THE INVENTION

1. Field of the Invention

This invention relates to novel human interleukin-2 polypeptide derivatives, to recombinant plasmids with DNA fragments coding for said polypeptide derivatives being inserted therein, to microorganisms harboring said plasmids and to a method of producing human interleukin-2 polypeptide derivatives using said microorganisms.

2. Description of the Prior Art

Interleukin-2 (hereinafter abbreviated as IL-2) is a lymphokine produced by T lymphocytes. Binding of the receptors on the surface of activated T-cells, IL-2 is not only essential for proliferation of antigen-stimulated T cells but also bestowed with physiological activities, such as the ability to enhance the generation of cytotoxic T lymphocytes and the ability to activate natural killer (NK) cells. Accordingly, IL-2 is expected to be useful in clinical applications for the treatment of immunodeficiency syndrome or for antitumor immunotherapy. The human IL-2 polypeptide derivatives according to the invention also have IL-2 activity and are expected to be useful as drugs in the same way as IL-2.

The rapid progress in recombinant DNA technology in recent years has made it possible to produce in large quantities in microorganisms those substances that are produced only in small quantities in eukaryotic cells and accordingly are difficult to isolate.

The nucleotide sequence of the cDNA coding for IL-2 has been determined by Taniguchi et al. through cloning, in *Escherichia coli*, of a cDNA derived from the human T-cellular leukemia cell line Jurkat-111 and by Shimada et al. through cloning of a human tonsillar cellderived cDNA in *Escherichia coli* [Taniguchi et al.: Nature, 302, 305 (1983); Shimada et al.: Biochem. Biophys. Res. Commun., 115, 1040 (1983)]. When the IL-2 DNA cloned by Shimada et al is inserted into the tryptophan promotercontaining vector pKYP10 (U.S. patent application Ser. No. 06/452,290 corresponding to Published Unexamined Japanese Patent Application No. 110600/83) and expressed in *Escherichia coli*, the IL-2 can be produced in large quantities.

The IL-2-encoding cDNA cloned by Shimada et al. has the nucleotide sequence shown in FIG. 1.

As for IL-2 derivatives, it is reported that substitution of serine (Ser) for the 58th amino acid cysteine (Cys) or Ser for the 105th amino acid cysteine leads to a reduction in specific activity to 1/50 to 1/100 of that of the parent IL-2. Substitution of Ser for the 125th amino acid Cys is said to increase in specific activity by 30% [A. Wang et al.: Science, 224, 1431 (1984)].

SUMMARY OF THE INVENTION

It is an object of the present invention to provide means for producing polypeptides having high IL-2 activity at low cost and in large quantities.

The present inventors have found that IL-2 derivatives having high IL-2 activity can be produced when the cDNA for IL-2, as shown in FIG. 1 is modified by deletion of one or more amino acids, preferably near the N-terminus, from the usual amino acid sequence of the human IL-2 polypeptide and a cloned *Escherichia coli* strain harboring a plasmid containing the modified DNA is cultivated. The present invention has now been completed based on this finding.

The invention thus provides novel human IL-2 polypeptide derivatives, recombinant plasmids with DNAs coding for said polypeptide derivatives inserted therein, microorganisms harboring said plasmids and a method of producing novel human IL-2 polypeptide derivatives using said microorganisms. The human IL-2 polypeptide derivatives of the present invention are characterized by deletion of at least one amino acid from the amino acid sequence of the human IL-2 polypeptide as shown in FIG. 1.

BRIEF DESCRIPTION OF THE DRAWINGS

In the accompanying drawings,

FIG. 1 shows the amino acid sequence of the human IL-2 polypeptide and nucleotide sequence coding for the peptide;

FIG. 5 shows the amino acid sequence of the human IL-2 polypeptide and nucleotide sequence coding for the peptide absent the 20 amino acid presequence, the novel IL-2 polypeptides of this invention having at least two amino acids deleted from among the first to the fifth amino acid in the amino acid sequence show in this Figure.

DETAILED DESCRIPTION OF THE INVENTION

Figure 2:
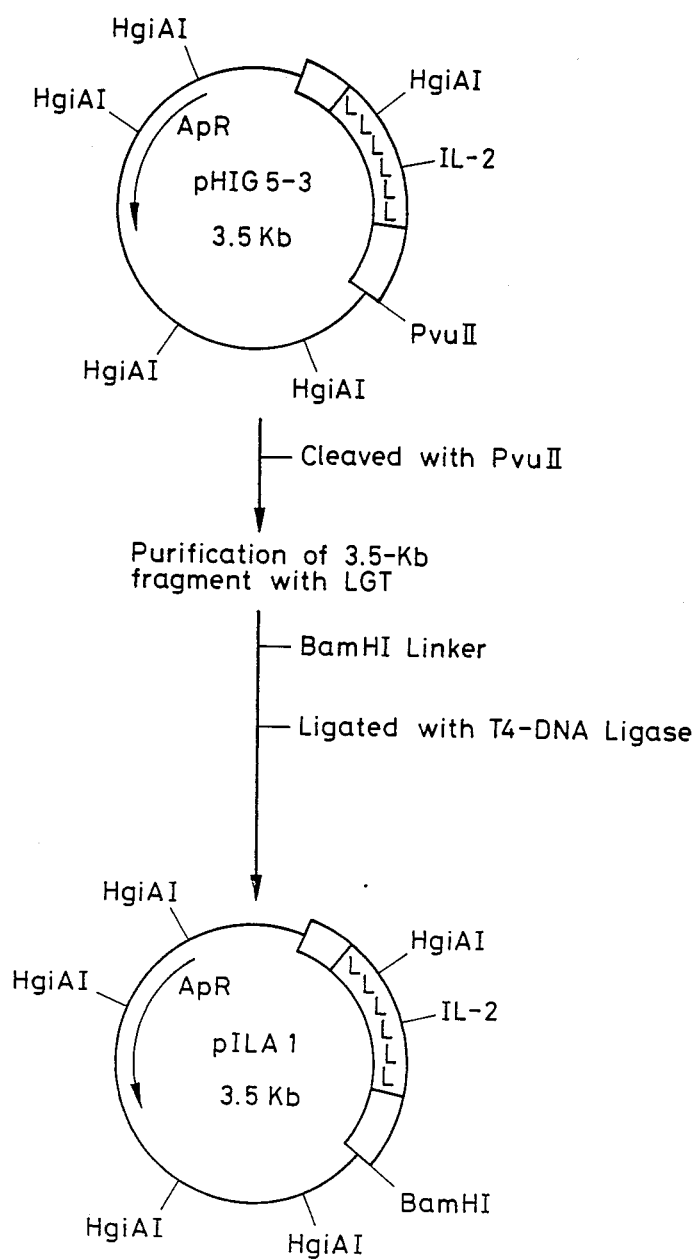
FIG. 2 shows the construction scheme for the plasmid pILA1.

The human IL-2 polypeptide derivatives according to the present invention are characterized by deletion of at least one amino acid from the amino acid sequence of the human IL-2 polypeptide as shown in FIG. 1. The amino acid deletion consists in the deletion of one or more amino acids occurring in the neighborhood of the N-terminus, and preferably at least one (and as many as all of the amino acids) of the first to fifth amino acids from the N-terminus is(are) deleted.

The recombinant plasmids according to the invention are plasmids derived by inserting DNA fragments coding for the above human IL-2 polypeptide derivatives into an appropriate plasmid with DNA expression capability.

The DNA fragments coding for the human IL-2 polypeptide derivatives according to the invention should preferably have a sequence such that at least three bases out of the first to fifteenth bases in the DNA nucleotide sequence coding for human IL-2 as shown in FIG. 1 are missing.

The cDNA (human IL-2 cDNA) obtained by reverse transcription from the IL-2-encoding messenger RNA by using recombinant DNA techniques or the IL-2-encoding DNA obtained from chromosomal DNA may be used as the DNA coding for human IL-2 as shown in FIG. 1.

Any cDNA coding for human IL-2 may be used as the human IL-2 cDNA and a typical, useful example is pHIG5-3. pHIG5-3 is a plasmid reported by Shimada et al. and a method of producing the same is described by Shimada et al. in Biochem. Biophys. Res. Commun., 115, 1040 (1983).

The IL-2 DNA in pHIG5-3 has the nucleotide sequence shown in FIG. 1 as determined by the method of Maxam-Gilbert [Methods in Enzymology, 65, 499 (1980)].

Any suitable plasmid may be used as the plasmid for insertion thereinto of a DNA coding for an IL-2 polypeptide derivative according to the invention provided that said DNA can be expressed in *Escherichia coli*. Preferably, the foreign DNA can be inserted downstream from an appropriate promoter, such as the trp or lac promoter, and furthermore a plasmid with the distance between the Shine-Dalgarno sequence (hereinafter abbreviated as "SD sequence") and the initiation codon (ATG) adjusted adequately, for example to 6-18 base pairs can be used. More specifically, the plasmids pKYP10, pKYP11 and pKYP12 constructed by the present inventors (as described in U.S. patent application Ser. No. 06/452,290 corresponding to Published Unexamined Japanese Patent Application No. 110600/83, the disclosure of which is hereby incorporated by reference), among others, may be mentioned as preferred examples of plasmids suited to the insertion of the DNA. To provide the DNA coding for the IL-2 polypeptide derivative with the initiation codon, a plasmid having the initiation codon downstream from the promoter and allows the initiation codon to remain on the 3'-end side upon restriction enzyme cleavage. More specifically, pTrS3 (U.S. patent application Ser. No. 06/619,161 corresponding to Published Unexamined Japanese Patent Application Nos. 67297/84 and 140883/84) may be mentioned as a preferred example.

In the following, an example is given in which a recombinant plasmid containing a DNA coding for a human IL-2 polypeptide derivative is constructed using pHIG5-3 as the source of human IL-2 cDNA, pKYP10 as the plasmid for insertion of said DNA, and pTrS3 as the plasmid for providing the initiation codon.

DETAILED DESCRIPTION OF THE DRAWINGS AND GENERAL PREPARATION SCHEME

As shown in FIG. 2, pHIG5-3 [about 3.5 kilobases (hereinafter abbreviated as "kb")] is cleaved with Pvu II and a BamHI linker [10 base pairs (hereinafter abbreviated as "bp")] is introduced into the cleavage site to give pILA1 (about 3.5 kb).

Figure 3:
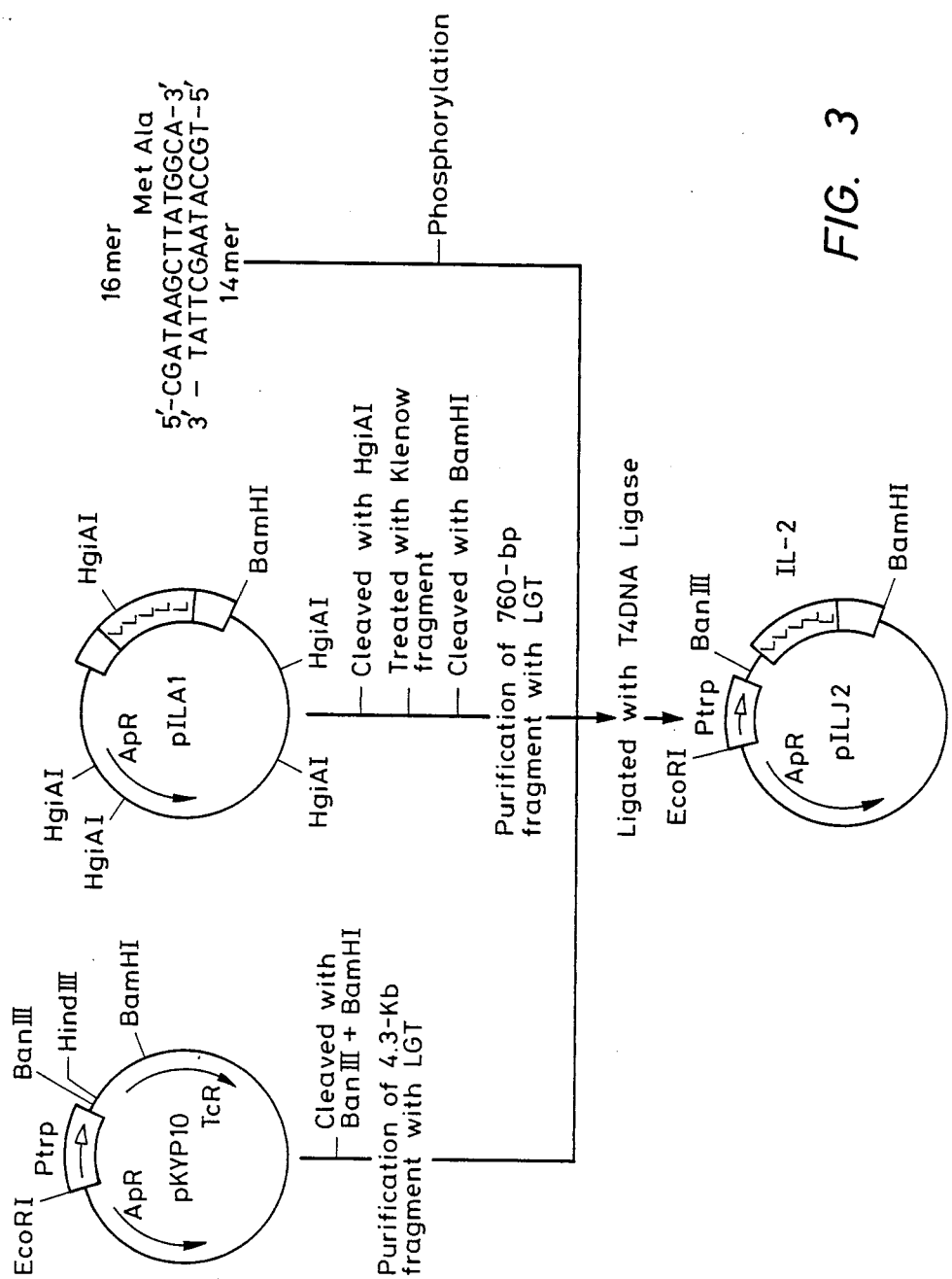
FIG. 3 shows the construction scheme for the plasmid pILJ2.

Then, pILA1 is cleaved with HgiAI, rendered blunt-ended by treatment with Klenow fragment, and further cleaved with BamHI. An about 760-bp DNA fragment is recovered and purified by low-gelling-temperature agarose gel electrophoresis (LGT method). Then, as shown in FIG. 3, pKYP10 is cleaved with BanIII and BamHI and an about 4.3-kb DNA fragment is recovered and purified. Both the DNA fragments thus obtained and the synthetic DNA shown in FIG. 3 [containing the initiation codon (ATG) and the codon GCA coding for the first amino acid alanine (Ala)] are ligated together in the presence of T4 DNA ligase to give pILJ2.

Figure 4:
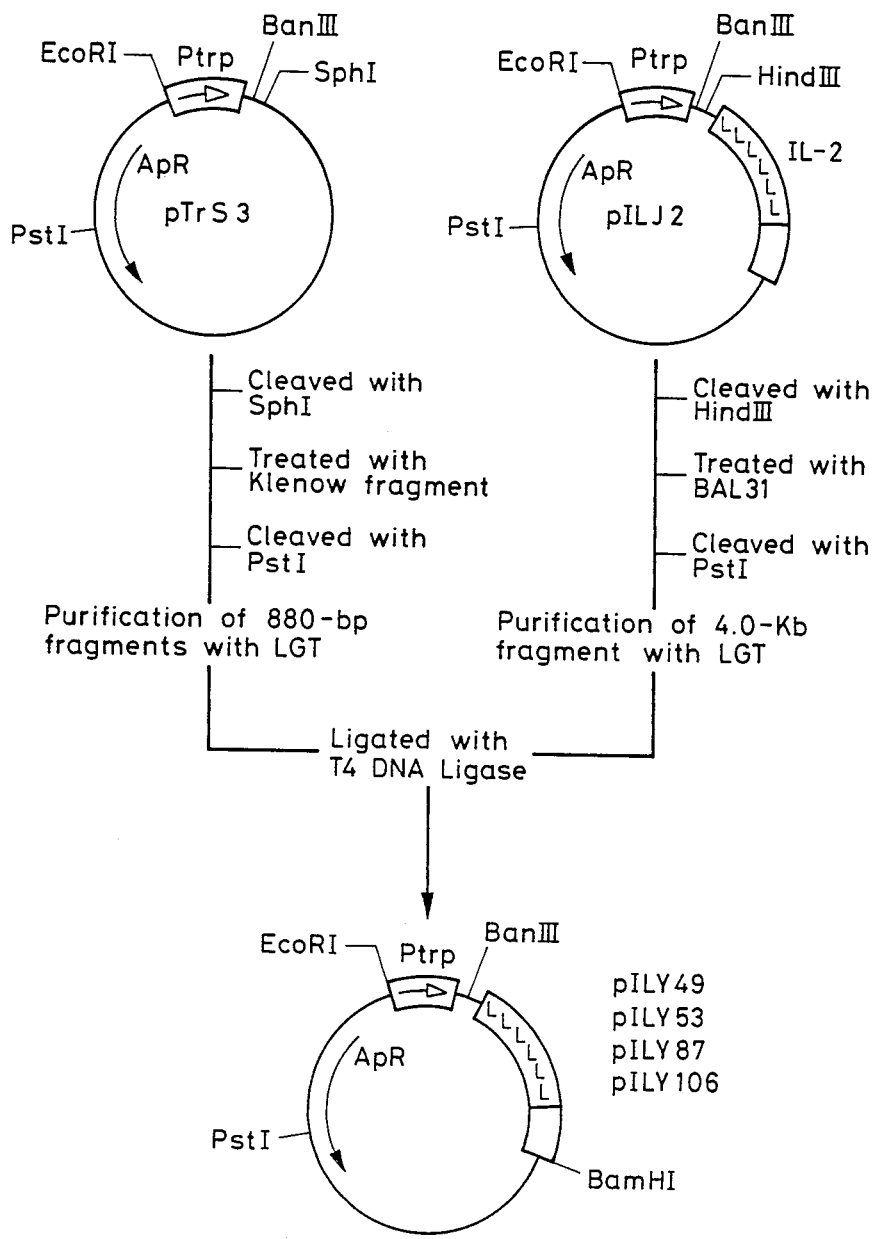
FIG. 4 shows the construction schemes for the plasmids pILY49, pILY53, pILY87 and pILY106.

For constructing a DNA coding for an Nterminally deficient IL-2 polypeptide derivative, pILJ2 is cleaved with HindIII, then treated with BAL31 for a short period of time (1-30 minutes) to thereby pare off the DNA coding for one or more N-terminal amino acids of IL-2, and further cleaved with PstI, as shown in FIG. 4, and an about 4.0-kb DNA fragment is recovered and purified. Separately, the initiation codon-containing vector pTrS3 is cleaved with SphI, then treated with Klenow fragment and further cleaved with PstI, and an 880-bp DNA fragment is recovered and purified.

Both the DNA fragments are ligated together using T4 ligase to give a recombinant plasmid with a DNA coding for a human IL-2 polypeptide derivative inserted therein. The four plasmids obtained in the examples that follow were named pILY49, pILY53, pILY87 and pILY106.

The reaction conditions for the above-mentioned recombinant DNA techniques are generally as follows:

The DNA digestion with restriction enzymes is generally carried out in a reaction medium containing 2-200 mM (preferably 10-40 mM) Tris-HCl (pH 6.0-9.5, preferably 7.0-8.0), 0-200 mM NaCl and 2-20 mM (preferably 5-10 mM) $MgCl_2$ at 20°-70° C. (the optimal temperature may vary depending on the restriction enzyme used) for 15 minutes to 24 hours, using 0.1-20 μg of DNA and 0.1-100 units (preferably 1-3 units) of restriction enzyme per μg of DNA. The reaction is terminated generally by heating at 55°-75° C. for 5-30 minutes. The restriction enzymes may also be inactivated with a reagent such as phenol or diethylpyrocarbonate.

DNA fragments produced by restriction enzyme digestion are purified by low-gelling-temperature agarose gel electrophoresis (LGT method) [L. Wieslander: Analytical Biochemistry, 98, 305 (1979)] or by polyacrylamide gel electrophoresis [A.M. Maxam et al.: Proc. Natl. Acad. Sci. USA, 74, 560 (1977)], for instance.

The ligation of DNA fragments is carried out in a reaction medium containing 2-200 mM (preferably 10-40 mM) Tris-HCl (pH 6.1-9.5, preferably pH 7.0-8.0), 2-20 mM (preferably 5-10 mM) $MgCl_2$, 0.1-10 mM (preferably 0.5-2.0 mM) ATP and 1-50 mM (preferably 5-10 mM) dithiothreitol at 1°-37° C. (preferably 3°-20° C.) for 15 minutes to 72 hours (preferably 2-20 hours), using 0.3-10 units of T4 DNA ligase.

The recombinant plasmid DNA resulting from the ligation reaction is introduced into *Escherichia coli*, using the transformation method of Cohen et al. [S. N. Cohen et al.: Proc. Natl. Acad. Sci. USA, 69, 2110 (1972)], as necessary.

DNA isolation from a recombinant plasmid DNA-carrying *Escherichia coli* transformant is carried out by the method described later herein in Example 1 or the method of Birnboim et al. [H. C. Birnboim et al.: Nucleic Acids Res., 7, 1513 (1979)], for instance.

The plasmid DNA is examined for restriction enzyme cleavage sites by digestion with 1-10 restriction enzymes followed by agarose gel electrophoresis or polyacrylamide gel electrophoresis. If necessary, the nucleotide sequence of the DNA is further determined by the method of Maxam-Gilbert [Proc. Natl. Acad. Sci. USA, 74, 560 (1977)].

Desired recombinant plasmid DNAs can be produced under conditions such as mentioned above.

The IL-2 polypeptide derivatives according to the invention can be produced in the following manner:

A competent plasmid (e.g. pILY49) is used to transform *Escherichia coli* K12 HB101. When pILY49 is used, a pILY49-carrying *Escherichia coli* transformant is selected from among ampicillin-resistant($Ap^R$) colonies. The pILY49-carrying *Escherichia coli* transformant is cultivated in an appropriate medium, whereby the desired IL-2 polypeptide derivative can be provided in the culture.

Any synthetic or natural medium may be used as the medium mentioned above provided that it is suited for the growth of *Escherichia coli* and for the IL-2 polypeptide derivative production.

Usable as the carbon source are glucose, fructose, lactose, glycerol, mannitol and sorbitol, among others. Examples of the nitrogen source are $NH_4Cl$, $(NH_4)_2SO_4$, casamino acids, yeast extract, polypeptone, meat extract, Bacto-tryptone and corn steep liquor. Other nutrient sources which are usable include $K_2HPO_4$, $KH_2PO_4$, NaCl, $MgSO_4$, vitamin $B_1$, $MgCl_2$ and so on.

The cultivation is conducted at pH 5.5-8.5 and at a temperature of 18°-40° C. with aeration and stirring. The accumulation of the human IL-2 polypeptide derivative in bacterial cells becomes detectable after 5-90 hours of cultivation. Cells are then harvested from the culture and disrupted by sonication. Centrifugation gives a sediment (cell pellet). Using the method of Marston et al. [F. A. O. Marston et al.: BI/TECHNOLOGY, 2, 800 (1984)], the IL-2 polypeptide derivative is extracted from the sediment, purified, solubilized and renatured. The biological activity of the human IL-2 derivative is determined by the method of Gillis et al. [S. Gillis et al.: J. Immunol., 120, 2027 (1978)].

In accordance with the invention, IL-2 polypeptide derivatives having higher IL-2 activity as compared with natural IL-2 can be microbially produced at low cost and in large quantities.

The following examples are further illustrative of the present invention.

EXAMPLE 1

Construction of the plasmid pILA1 having a BamHI site downstream from the IL-2 gene depicted in the construction scheme of FIG. 2:

The 3.5-kb plasmid pHIG5-3 (2 μg) was dissolved in a total volume of 50 μl of a buffer containing 20 mM Tris-HCl (pH 7.5), 10 mM $MgCl_2$, 10 mM dithiothreitol and 50 mM NaCl (hereinafter referred to as "Y-50 buffer"), and 4 units of the restriction enzyme PvuII (Takara Shuzo; hereinafter, unless otherwise specified, all the enzymes used were products of Takara Shuzo) were added. A digestion reaction was carried out at 37° C. for 2 hours. An about 3.5-kb pHIG5-3 fragment (1 μg) was isolated from the reaction mixture by the LGT method. This DNA fragment (0.1 μg) was ligated in the presence of 5 picomoles of a 5'-phosphorylated BamHI linker (5'-pCCGGATCCGG-3'; from Collaborative Research) in 20 μl of a buffer containing 20 mM Tris-HCl (pH 7.6), 10 mM $MgCl_2$, 10 mM dithiothreitol and 1 mM ATP (hereinafter referred to as "T4 ligase buffer"), with 2 units of T4 ligase added, at 4° C. for 18 hours. The thus-obtained recombinant plasmid DNA was used to transform *Escherichia coli* K12 HB101 [Boliver et al.: Gene, 2, 75 (1977)] by the method of Cohen et al. [S. N. Coehn et al.: Proc. Natl. Acad. Sci. USA, 69, 2110 (1972)] (hereinafter, this method was always used for transforming *Escherichia coli*) to give $Ap^R$ colonies. The plasmid DNA was isolated from such transformant strain by the method of Birnboim et al. [H.C. Birnboim et al.: Nucleic Acids Res., 7, 1513 (1979)] (hereinafter, this method was always used for plasmid DNA isolation) and purified. The plasmid structure was analyzed by digesting the plasmid DNA with BamHI and other restriction enzymes. It was confirmed that a recombinant plasmid derived from pHIG5-3 by insertion of the BamHI linker at the PvuII site had been obtained. This plasmid was named pILA1.

EXAMPLE 2

Construction of the IL-2 expression plasmid pILJ2 according to the scheme of FIG. 3:

The pILA1-harboring *Escherichia coli* K12 HB101 strain obtained in Example 1 was cultivated and the pILA1 DNA was prepared from the cultured bacterial cells by the method of Birnboim et al. A 10-μg portion of the pILA1 DNA obtained was dissolved in a total volume of 50 μl of a buffer containing 20 mM Tris-HCl (pH 7.5), 10 mM $MgCl_2$, 10 mM dithiothreitol and 150 mM NaCl, 10 units of the restriction enzyme HgiAI (New England Biolabs) were and cleavage reaction was carried out at 37° C. for 4 hours. A DNA fragment (9 μg) was recovered by extraction with phenol, extraction with chloroform and precipitation with ethanol. This DNA fragment was dissolved in 100 μl of a buffer containing 50 mM Tris-HCl (pH 7.8), 7 mM $MgCl_2$ and 6 mM mercaptoethanol, dATP, dTTP, dCTP and dGTP were added each to a concentration of 1 mM and, further, 4 units of Klenow fragment (Takara Shuzo) were added. Reaction was conducted at room temperature for 1 hour to thereby pare off the cohesive ends. A DNA fragment (8 μg) was recovered by phenol extraction, chloroform extraction and ethanol precipitation. The DNA fragment was dissolved in a total volume of 40 μl of a buffer containing 20 mM TrisHCl (pH 7.5), 10 mM $MgCl_2$, 10 mM dithiothreitol and 100 mM NaCl (hereinafter referred to as "Y-100 buffer"), 10 units of BamHI were added, and cleavage reaction was performed at 37° C. for 2 hours. An about 760-bp DNA fragment (HgiAIKlenow fragment-BamHI fragment) containing a major portion of the human IL-2 DNA (about 0.5 μg) was obtained from the reaction mixture by the LGT method.

Separately, 3 μg of pKYP10 prepared by the method described in U.S. patent application Ser. No. 06/452,920 corresponding to Published Unexamined Japanese Patent Application No. 110600/83 was dissolved in 50 μl of Y-100 buffer, the restriction enzymes BamHI and BanII (each 5 units; Toyobo) were added, and cleavage reaction was conducted at 37° C. for 4 hours. An about 4.3-kb DNA fragment (about 1.8 μg) containing the tryptophan promoter (Ptrp) was isolated from the reaction mixture by the LGT method.

Further, separately, for reasons such as the necessity of providing a codon (GCA) for alanine, which is the N-terminus of the mature human IL-2 polypeptide, the initiation codon (ATG) necessary for expression and the necessity of adjusting the distance between the SD sequence downstream from Ptrp and ATG to an adequate length within the range of 6-18 bp, the following DNA linker was synthesized:

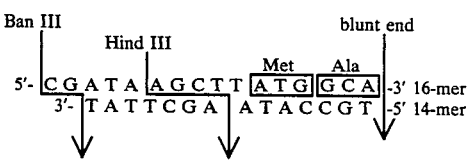

First, the single-stranded DNAs, i.e. the 16-mer and 14-mer, were synthesized by the usual phosphotriester method [R. Crea et al.: Proc. Natl. Acad. Sci. USA, 75, 5765 (1978)]. The 16-mer and 14-mer (each 2 μg) were dissolved in a total volume of 40 μl of a buffer containing 50 mM Tris-HCl (pH 7.5), 10 mM $MgCl_2$, 5 mM dithiothreitol, 0.1 mM EDTA and 1 mM ATP, 30 units of T4 polynucleotide kinase (Takara Shuzo) were added, and phosphorylation reaction was carried out at 37° C. for 60 minutes.

Then, 0.4 μg of the pILAI-derived HgiAI-Klenow fragment-BamHI fragment (about 760 bp) obtained above and 1.0 μg of a BanIII-BamHI fragment (about 4.3 kb) of the expression vector pKYP10 were dissolved in 25 μl of T4 ligase buffer and, to this mixed solution, there was added about 0.1 μg of the above-mentioned DNA linker, followed by the further addition of 6 units of T4 DNA ligase. A ligation reaction was carried out at 4° C. for 18 hours.

The thus-obtained recombinant plasmid mixture was used to transform *Escherichia coli* (K12 HB101, and an Ap$^R$ colony was obtained. The plasmid DNA was recovered from cells obtained by cultivating this colony. The structure of the plasmid obtained was established by cleavage with EcoRI, BanIII, HindIII and BamHI followed by agarose gel electrophoresis. This plasmid was named pILJ2. The nucleotide sequence in the neighborhood of the BanIII and HindIII sites of pILJ2 as confirmed by the method of Maxam-Gilbert [A. M. Maxam et al.: Proc. Natl. Acad. Sci. USA, 74, 560 (1977)]is as follows:

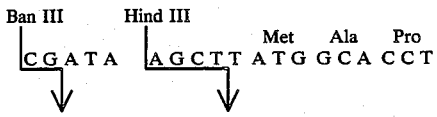

EXAMPLE 3

Construction of the plasmids pILY49, pILY53, pILY87 and pILY106 coding for polypeptides otherwise equal to human IL-2 but lacking in an N-terminal portion thereof, as depicted in FIG. 4, was as follows:

The plasmid pILJ2 (about 5.1 kb; 25 μg) obtained by the procedure of Example 2 was dissolved in 400 μl of Y-100 buffer, 50 units of HindIII were added, and a reaction was conducted at 37° C. for 3 hours. To an 80-μl portion (containing 5 μg of DNA) of the reaction mixture were added 24 μl of 5 times concentrated BAL31 buffer [100 mM Tris-HCl (pH 8.1), 3 M NaCl, 60 mM CaCl$_2$, 60 mM MgCl$_2$, 5 mM EDTA] and 16 μl of water, followed by the further addition of 0.25 unit of the nuclease BAL31 [Bethesda Research Laboratories (BRL)]. Reaction was carried out at 30° C. for 1 minute. The nuclease BAL31 can cleave nucleotides from the end of a DNA molecule (exonuclease activity), and, under the above-mentioned reaction conditions, about 30 base pairs can be pared off from the HindIII site. For DNA recovery, the reaction mixture was subjected to phenol extraction, followed by chloroform extraction and ethanol precipitation. A 1.0-μg portion of the thus-recovered pILJ2-HindIII-BAL31 fragment fraction was dissolved in 20 μl of Y-100 buffer, 2 units of PstI were added, and cleavage reaction was carried out at 37° C. for 2 hours. An about 4.0-kb DNA fragment fraction (pILJ2-HindIII-BAL31-PstI fragment; 0.5 μg) was recovered from the reaction mixture by the LGT method.

Separtely, 8.0 μg of the ATG expression vector pTrS3 (3.8 kb) was dissolved in 80 μl of Y-50 buffer, 15 units of SphI (BRL) were added, and a cleavage reaction was carried out at 37° C. for 3 hours. A 3.8-kb DNA fragment (5.0 μg) was recovered in a purified form from the reaction mixture by the LGT method.

This 3.8-kb DNA fragment (5.0 μg) was dissolved in 100 μl of a buffer containing 50 mM Tris-HCl (pH 7.8), 7 mM MgCl$_2$ and 6 mM mercaptoethanol, dATP, dTTP, dCTP and dGTP were added each to a concentration of 1 mM, 5 units of Klenow fragment were further added, and the reaction was conducted at room temperature for 1 hour to thereby pare off the cohesive ends. Phenol extraction, chloroform extraction and ethanol precipitation gave 3.0 μg of a DNA fragment. The thus-recovered DNA fragment (3.0 μg) was dissolved in a total volume of 30 μl of Y-100 buffer, 5 units of PstI were added, and cleavage reaction was carried out at 37° C. for 3 hours. An about 880-bp DNA fragment containing Ptrp (pTrS3-SphI-Klenow fragment-PstI fragment; 0.5 μg) was recovered from the reaction mixture by the LGT method.

Both the DNA fragments obtained, namely the pILJ2-HindIII-BAL31-PstI fragment (about 4.0 kb; 0.5 μg) and pTrS3-SphI-Klenow fragment-PstI fragment (880 bp; 0.5 μg), were dissolved in a total volume of 20 μl of T4 ligase buffer, 0.3 unit of T4 DNA ligase was added, and ligation reaction was carried out at 4° C. for 18 hours.

The recombinant plasmid mixture thus obtained was used to transform *Escherichia coli* HB101, and plasmid DNAs were recovered from cells obtained by cultivating the Ap$^R$ colonies obtained. The plasmids were named pILY49, pILY53, pILY87 and pILY106, respectively, as shown in FIG. 4. The structure of each of these plasmids was confirmed by cleavage with BanIII, BamHI and EcoRI followed by agarose gel electrophoresis. The respective nucleotide sequences in the neighborhood of the N-terminus of the structural gene for human IL-2 which occur in the above plasmids were confirmed by the method of Maxam-Gilbert to be as follows:

```
                    Met  Thr  Gln  Leu  Gln
For pILY49:  A T G  ACA  CAG  CTA  CAA
                    Met  Ser  Thr  Lys  Lys
For pILY53:  A T G  TCT  ACA  AAG  AAA
                    Met  Lys  Thr  Gln  Leu
For pILY87:  A T G  AAA  ACA  CAG  CTA
                    Met  Ser  Ser  Ser  Thr
For pILY106: A T G  TCA  AGT  TCT  ACA
```

Thus, it was established that the IL-2 polypeptide derivative encoded by pILY49, named IL-2(Δ1-9), is deficient in the nine amino acids from the N-terminal Ala to the 9th amino acid Lys as compared with the mature human IL-2 polypeptide but starts with the 10th amino acid Thr. Similarly, the IL-2 polypeptide derivative encoded by pILY53, named IL-2(Δ1-5), was confirmed to be deficient in the five amino acids from the N-terminus, the IL-2 polypeptide derivative encoded by pILY87, named IL-2(Δ1-8), to be deficient in the eight amino acids from the N-terminus, and the IL-2 polypeptide derivative encoded by pILY106, named IL-2(Δ1-3), to be deficient in the three amino acids from the N-terminus.

EXAMPLE 4

Production of IL-2 derivatives in Escherichia coli strains harboring pILJ2, pILY49, pILY53, pILY87 and pILY106, respectively:

*Escherichia coli* K12 HB101 strains harboring the recombinant plasmids obtained in Example 2 and Example 3, namely pILJ2, pILY49, pILY53, pILY87 and pILY106, respectively, were named EILJ2, EILY49, EILY53, EILY87 and EILY106, respectively, and each was cultivated in LG medium (prepared by dissolving 10 g of Tryptone, 5 g of yeast extract, 5 g of NaCl and 2 g of glucose in one liter of water and adjusting the pH to 7.0 with NaOH) at 37° C. for 18 hours. A 0.5 ml portion of the culture was used to inoculate 10 ml of MCG medium (0.6% Na$_2$HPO$_4$, 0.3% KH$_2$PO$_4$, 0.5% NaCl, 0.5% casamino acids, 1 mM MgSO$_4$, 4 μg/ml vitamin B$_1$, pH 7.2) and, after cultivation at 30° C. for 4–8 hours, 3 β-indolylacrylic acid (hereinafter abbreviated as IAA) was added to a concentration of 10 μg/ml. Cultivation was continued further for 2–12 hours. Cells were harvested by 10-minute centrifugation at 8,000 rpm and washed with 30 mM Nacl-30 mM Tris-HCl buffer (pH 7.5). The washed cells were suspended in 3 ml of the above buffer and disrupted by sonication at 0° C. (Branson Sonic Power Company's Sonifier Cell Disruptor 200, output control 2, 10 minutes). The disrupted cells were centrifuged at 15,000 r.p.m. for 30 minutes and the cellular sediment was recovered. In the conventional manner, by using the method of Marston et al. [F. A. D. Marston et al.: BIO/TECHNOLOGY, 2, 800 (1984)], the IL-2 polypeptide derivative was extracted from the sediment, purified, solubilized and renatured, and assayed for human IL-2 activity by the method of Gillis et al. [S. Gillis et al.: J. Immunol., 120, 2027 (1978)]. For the protein assay, Nippon Bio-Rad Laboratories' protein assay kit (standard assay method) [M. M. Bradford: Anal. Biochem., 72, 248 (1976)] was used.

The results thus obtained are shown in Table 1.

TABLE 1

| Strain | harbored | Product encoded by plasmid | Relative specific IL-2 activity* |
|---|---|---|---|
| EILJ2 | pLJ2 | IL-2 | 100 |
| EILY106 | pILY106 | IL-2(Δ1–3) | 125 |
| EILY53 | pILY53 | IL-2(Δ1–5) | 130 |

TABLE 1-continued

| Strain | harbored | Product encoded by plasmid | Relative specific IL-2 activity* |
|---|---|---|---|
| EILY87 | pILY87 | IL-2(Δ1–8) | 67 |
| EILY49 | pLY49 | IL-2(Δ1–9) | 48 |

*The specific activity of intact IL-2 was taken as 100.

The *Escherichia coli* strains harboring pILY53 and pILY106, namely *Escherichia coli* EILY53 (FERM BP-748) and *Escherichia coli* EILY106 (FERM BP-747) have been deposited at the Fermentation Research Institute, Agency of Industrial Science and Technology, Japan since March 26, 1985 under the Budapest Treaty.

The invention also includes (1) methods of treating immunodeficiency syndromes comprising administering to a person having an immunodeficiency syndrome an effective, immuno-restoring amount of the novel human IL-2 peptide derivative of this invention, and (2) methods of treating tumors immunologically comprising administering to a person having a tumor susceptible to treatment an effective amount of a novel human IL-2 polypeptide derivative according to the present invention.

While the invention has been described in detail and with reference to specific embodiments thereof, it will be apparent to one skilled in the art that various changes and modifications can be made therein without departing from the spirit and scope thereof.

What is claimed is:

1. A human interleukin-2 polypeptide derivative derived from the human interleukin-2 polypeptide having the amino acid sequence wherein at least three amino acids are deleted from among the first to fifth amino acid in the amino acid sequence shown in FIG. 5.

2. The polypeptide derivative of claim 1, in which all of the amino acids from the first to the fifth amino acids in the amino acid sequence shown in FIG. 5 are deleted.

3. The polypeptide derivative of claim 1, in which all of the amino acids from the first to the third amino acids in the amino acid sequence shown in FIG. 5 are deleted.

* * * * *